United States Patent [19]

Schimanski

[11] 4,214,146

[45] Jul. 22, 1980

[54] ELECTRICALLY HEATED VAPORIZER DEVICE FOR DISPENSING A THERMALLY VOLATILIZABLE SUBSTANCE

[75] Inventor: Georg Schimanski, Breckerfeld, Fed. Rep. of Germany

[73] Assignee: Globol-Werk GmbH, Neuburg, Fed. Rep. of Germany

[21] Appl. No.: 915,608

[22] Filed: Jun. 15, 1978

[30] Foreign Application Priority Data

Jul. 8, 1977 [DE] Fed. Rep. of Germany ....... 2730855

[51] Int. Cl.² .......................... A01M 1/20; A61L 9/02; F22B 1/28
[52] U.S. Cl. ..................................... 219/274; 43/129; 128/203.27; 219/275; 219/385; 219/521; 239/57; 239/136; 422/306
[58] Field of Search ................................. 219/271–276, 219/214, 521, 385–387; 422/125, 305, 306; 128/186, 192; 43/128, 129, 130, 125; 239/135, 133, 128, 34, 51.5, 53–60; 206/0.5; 221/150 R, 150 A

[56] References Cited

U.S. PATENT DOCUMENTS

| 900,292 | 10/1908 | Meredith | 219/521 X |
|---|---|---|---|
| 1,378,095 | 5/1921 | Case | 219/274 X |
| 1,801,538 | 4/1931 | Briscoe | 422/126 |
| 1,934,887 | 11/1933 | Robinson | 128/192 |
| 2,233,431 | 3/1941 | Robinson | 128/192 |
| 2,513,919 | 7/1950 | Costello | 422/306 |
| 2,599,485 | 6/1952 | Robinson | 219/271 X |
| 2,691,716 | 10/1954 | Wellens | 219/271 |
| 2,741,003 | 4/1956 | David | 219/274 X |
| 2,942,090 | 6/1960 | Diehl | 219/271 |
| 3,895,928 | 7/1975 | Moran | 239/136 X |

FOREIGN PATENT DOCUMENTS

| 2552901 | 6/1976 | Fed. Rep. of Germany . |
|---|---|---|
| 2552902 | 3/1977 | Fed. Rep. of Germany . |
| 936405 | 9/1963 | United Kingdom ..................... 219/271 |

Primary Examiner—A. Bartis
Attorney, Agent, or Firm—Karl F. Ross

[57] ABSTRACT

A device for dispensing a thermally volatilizable substance in which a housing is formed with a linear open-ended, open top guide channel extending across the upper portion thereof. A window is formed in the floor of the channel and a heater is disposed below the window, providing a support for a member impregnated with the volatilizable substance. A grid spans the open top of the guide channel above the window in juxtaposition therewith to permit release of the substance, e.g. an insecticide, while a skid or runner-shaped element carried by said grid presses the member against the heater. The impregnated member is slidably introduced into the channel through end open end thereof and when the volatilizable substance is exhausted, the member is ejected from the channel by the insertion of a new member into the channel.

10 Claims, 6 Drawing Figures

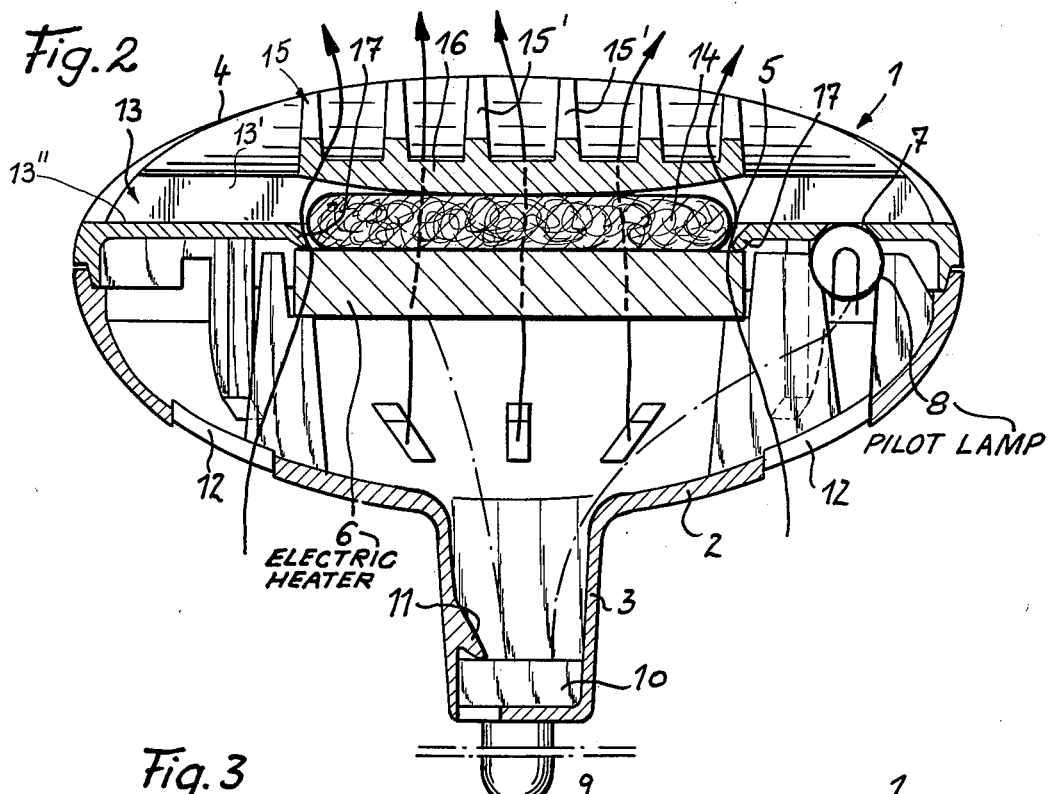
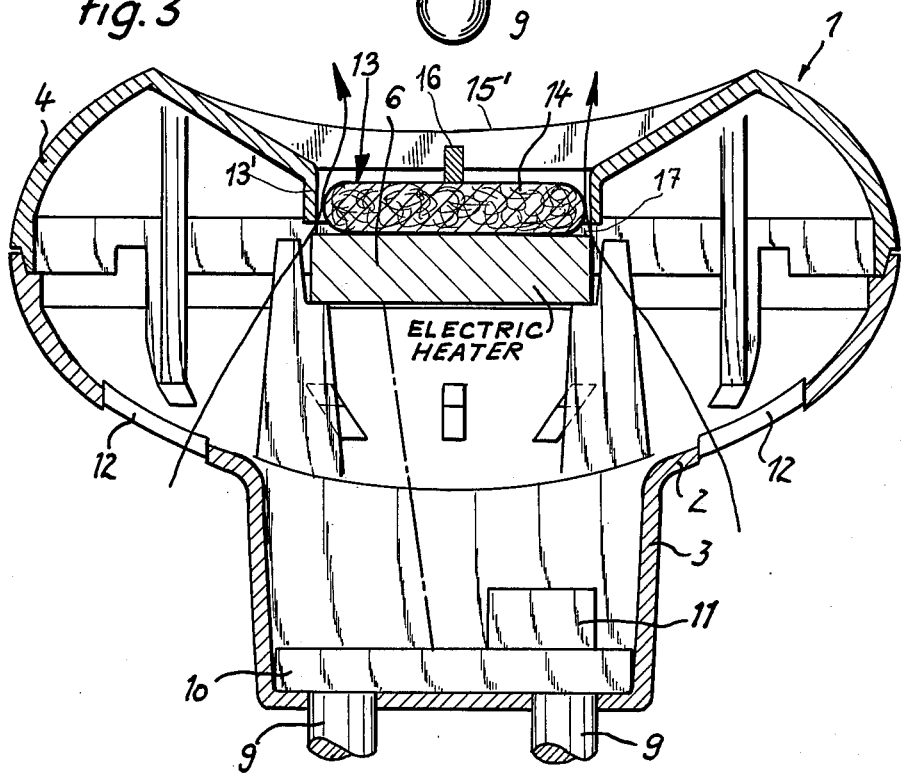

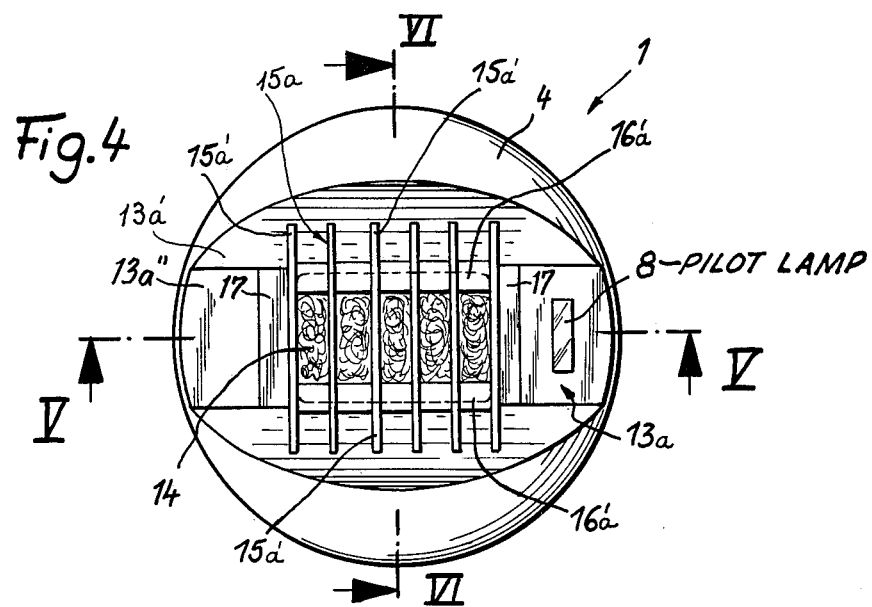
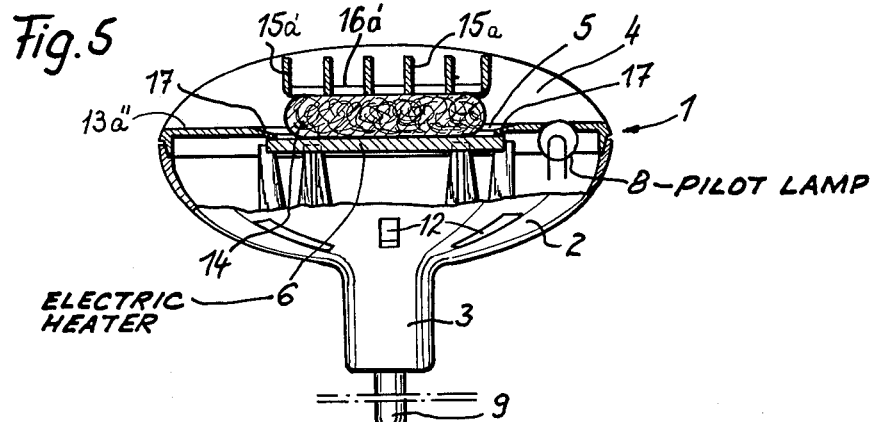
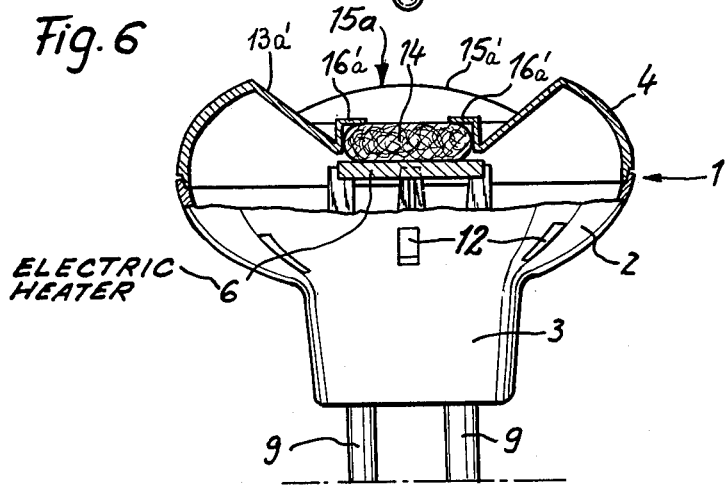

ELECTRICALLY HEATED VAPORIZER DEVICE FOR DISPENSING A THERMALLY VOLATILIZABLE SUBSTANCE

FIELD OF THE INVENTION

The present invention relates, in general, to dispensers, and, more specifically, to a dispenser for a thermally volatilizable substance such as an insecticide.

BACKGROUND OF THE INVENTION

Dispensers for insecticides are well known in the art and range from the active type to the passive type.

The active types of dispensers comprise aerosol cans containing an insecticide and propellant, or a liquid insecticide in a container with a manually operated or electrically operated pump, for driving the insecticide out in a mist or spray form.

The passive type of dispenser uses a container which is well ventilated and contains the insecticide in a solid or granular form which slowly volatilizes when exposed to the air.

There are several disadvantages in the known types of active dispensers. First, they dispense insecticide at a high rate, creating a heavy concentration of airborne insecticide in the vicinity of the user, which will inevitably be inhaled. Second, some of these dispensers require the handling of poisonous liquids by the user, which could be dangerous. Third, the aerosol can dispensers are not refillable, so they must be thrown away after they are exhausted.

There are also disadvantages to the passive type of dispensers. Their rate of volatilization is very slow and they are not effective for use in large areas because of this. Also, some of these dispensers are integral with the solid insecticide and are not reusable. Those that are reusable require disassembly for refilling while the solid or granular insecticide itself must be carefully packaged to prevent premature volatilization.

More specifically, it is known to provide a dispenser in which a volatizable material such as insecticide, may be driven by heating from a substrate in which the insecticide is adsorbed or absorbed, e.g. in the cellulosic material of the substrate. The same principle can be used for dispensing other materials from other solid substrates, the volatizable materials including air-cleaning agents, bactericides, disinfectants, cleaning agents and the like.

OBJECTS OF THE INVENTION

The principal object of the present invention is to provide a device for dispensing a thermally volatizable substance, such as an insecticide, an air-improving agent, a bactericide, a disinfectant, a deodorant or a cleaning substance from a solid plate or body of cellulose or other material in which the volatizable substance is stored, and which improves upon earlier devices for this purpose.

It is therefore an object of the present invention to provide a dispenser for an insecticide having an easily controlled output.

It is another object of the present invention to provide a dispenser for an insecticide which is easily refillable without disassembly.

It is still another object of the invention to provide a dispenser for an insecticide that uses a solid insecticide that will not volatilize automatically upon exposure to air.

It is yet a further object of the present invention to provide a dispenser for an insecticide which has no moving parts.

SUMMARY OF THE INVENTION

The above objects are realized in a dispenser for an insecticide in which a housing in the form generally of an oblate ellipsoid is formed with an open-ended, open top guide channel extending linearly across the upper portion thereof, with a window provided in the floor of the guide channel. Beneath this window there is provided an electric heater which forms a support for the solid insecticide, which is introduced through the guide channel, the heater also serving to raise the temperature of the insecticide to the volatilization point.

Spanning the open top of the channel, and juxtaposed to the window, there is formed a grid having a portion thereof engageable with the solid insecticide to press it against the heater for better and more even heat transfer and to hold it in position until the insecticide is exhausted and a new solid member is introduced, ejecting the exhausted member.

On the underside of the housing there are provided an array of vents which allows air to enter the hollow interior of the housing to maintain the heater at a temperature of 120° C. and to provide an airflow through the window. Also formed on the underside of the housing is an extension in the form of a hollow neck, centered on the minor axis of the oblate and provided with a pair of electrical contacts for supplying current to the heater and to a pilot light provided in the housing for indicating when the dispenser is operating.

The solid insecticide is in the form of a rectangular cellulose substrate, impregnated with a pyrethrum insecticide, formulated to volatilize at a temperature of about 120° C.

It should be pointed out that the invention need not be limited to the use of an electrical heater, but can use gas or some other fuel for generating heat, or even a catalytic heater which would operate in response to a particular formulation of the insecticide.

In its broadest outlines, the invention thus comprises a housing forming a channel through which the impregnated plate can be passed in succession (to replace a depleted plate with a plate fully charged with the volatizable substance), the housing being provided with a protective grid spaced above the planar heater and having an area corresponding at least to that of the heater and to the substance-carrying plate to be engaged with the heater. Indexing means can position the plate on the heater and the grid can be provided with runner-shaped members or a single runner-shaped member constituting a rib of the grid, to retain the impregnated plate against the heater. The system is dimensioned and of a configuration such that each impregnated plate can be fully inserted onto the heater and, upon the insertion of another plate to drive out the depleted plate, the latter will be fully discharged without entanglement with the grid. The runner may engage the edges of the plate or, where a single runner-shaped rib is provided, it can lie centrally of the plate so as to press the latter flat against the heater.

BRIEF DESCRIPTION OF THE DRAWING

The above and other objects, features and advantages of the invention will become more readily apparent from the following description, reference being made to the accompanying drawing, in which:

FIG. 2 is a sectional view taken along line II—II of FIG. 1;

FIG. 3 is a sectional view taken along line III—III of FIG. 1;

FIG. 4 is a top view similar to FIG. 1 of another embodiment of the invention;

FIG. 5 is a sectional view taken along line V—V of FIG. 4; and

FIG. 6 is a sectional view taken along line VI—VI of FIG. 5.

SPECIFIC DESCRIPTION

Figure 1:
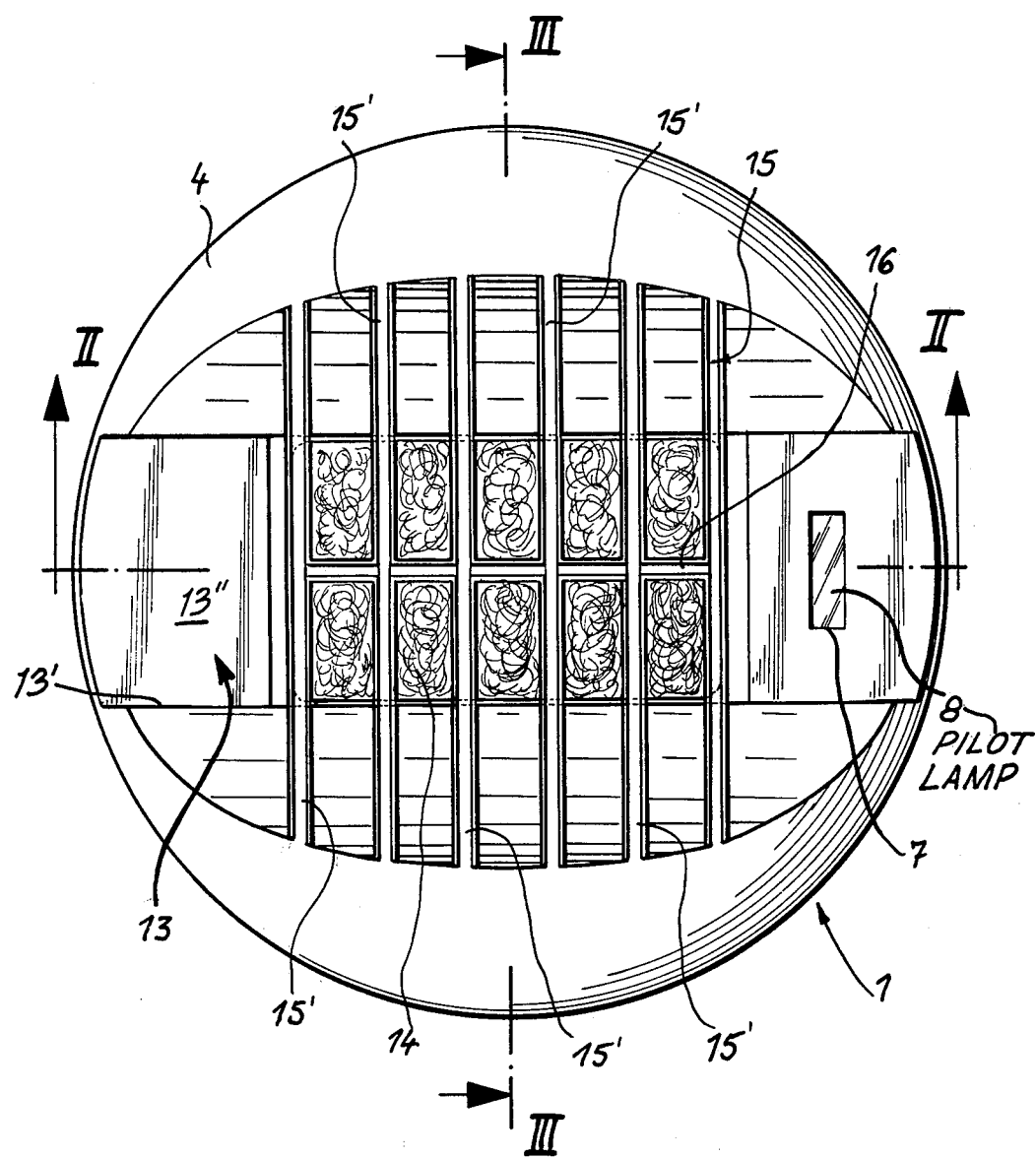
FIG. 1 is a top view of the dispenser according to the invention.

As can be seen in the drawing, a dispenser having a housing 1 in the form of an oblate, is defined by upper portion 4 and a lower portion 2, joined along the equator of the oblate.

As shown in FIGS. 1-3, an open-ended, open top guide channel 13 having a floor 13" flanked by vertical walls 13', is formed across the upper portion 4, along a diameter of the oblate. The floor 13" is formed with a window 5, below which is provided an electric heater 6, which forms a support for the solid insecticide-impregnated cellulose member 14, introduced through the channel 13. The window 5 is further provided with indexing means in the form of ramps 17, formed on the edges of the window 5 which are transverse to the channel 13. A screen grid 15 spans the open top of the channel 13 above window 5 and is juxtaposed thereto, the screen grid 15 being formed by slats 15', transverse to channel 13 and a single slat or runner 16, parellel to channel 13 and formed with an arcuate underside which engages the member 14 to prevent accidental dislodgement and to press the member 14 against the heater for good contact therewith. A smaller secondary window 7 is formed in the floor 13" of channel 13 and is provided with a pilot light 8 positioned therein for indicating when the dispenser is operating.

The lower portion 2 of housing 1 is formed with a downwardly extending projection 3, in which is seated an electrically insulated base 10, held in place by a pair of deflectable detents 11 (only one shown), formed on the projection 3 and flanking the base 10, which is provided with electrical contacts in the form of a pair of pins 9, connected to the heater 6 and pilot light 8. The lower portion 2 is further provided with an array of vents 12, which supply an air flow between the heater 6 and the window 5, which also serves to maintain the heater 6 at an operating temperature of 120° C.

In the embodiment shown in FIGS. 4 ∝ 6, the open-ended, open top guide channel 13a is defined by the floor 13a" and the sloping walls 13a' flanking the floor. In addition, the screen grid 15a has slats 15a' which have a somewhat different shape than those of FIGS. 1-3. The screen grid 15a is further provided with a pair of inverted L-shaped channels 16a', parallel to the channel 13a and flanking the floor 13a" thereof, engaging the insecticide member 14 along a portion of the sides and top. Aside from these differences, the remaining structure of the embodiment shown in FIGS. 4-6 is identical to the embodiment of FIGS. 1-3.

In operation, an insecticide member 14 is placed in the guide channel 13 or 13a and slid between the screen grid 15 or 15a and the heater 6, where the member 14 is positioned by the indexing ramps 17. The dispenser is then plugged into a source of electric current, heating the pyrethrum insecticide member 14 to a temperature of 120° C., volatilizing the pyrethrum insecticide through the screen grid. When the pyrethrum or other insecticide is exhausted from the substrate 14, a new member 14 is slid into the guide channel where it ejects the exhausted member 14 and becomes positioned on the heater. The exhausted members 14 can then be reimpregnated with insecticide and used again.

I claim:

1. A device for dispensing a thermally volatilizable substance, comprising:
   a hollow housing;
   an open-ended, open top linear guide channel having a planar floor extending from end to end formed across the upper portion of said housing;
   a window formed in the floor of said channel;
   a heater disposed beneath said window in alignment therewith and forming a support for a member introduced into said channel through an open end thereof and containing a volatilizable substance;
   a protective grid secured to said housing and spanning the open top of said channel above said window and juxtaposed therewith so that said member can be inserted into said channel in a feed direction without removing said grid,; and
   at least one elongated runner on said grid extending linearly in said feed direction and engageable with said member introduced into said channel, for pressing said member against said heater.

2. The device defined in claim 1 further comprising:
   means forming downwardly sloping ramps at the edges of said window which lie transverse to said guide channel for positioning said member on said heater; and
   a plurality of slats formed on said grid and lying transverse to said channel.

3. The device defined in claim 1 wherein said heater is electric and is provided with a pilot light in circuit with said heater for indicating energization thereof.

4. The device defined in claim 3, further comprising:
   a projection on said housing; and
   a pair of electrical contacts connected to said heater and said pilot light for supplying current thereto, mounted on said projection.

5. The device defined in claim 4 wherein:
   said housing is generally an oblate ellipsoid;
   said channel is formed along a diameter of said housing;
   said projection is a hollow neck extending downwardly from the lower surface of said housing;
   said electrical contacts are a pair of pins formed on a base and held in position in said neck by a pair of deflectable detents formed on said neck and flanking said base; and
   said window is of rectangular configuration.

6. The device in claim 5 wherein said housing is formed in two pieces joined along the equator of said oblate.

7. The device defined in claim 6 wherein said runner is a narrow downwardly arcuate portion formed on the underside of said grid and parallel to said channel.

8. The device defined in claim 6 wherein two such runners are provided and comprise a pair of spaced apart inverted L-shaped channels formed on said protective grid and parallel to said guide channel for flanking said member along a portion of the sides and top thereof.

9. The device defined in claim 3 wherein said pilot light is positioned in a small window in the floor of said channel at a location visible through the open top of said channel when said member is operatively positioned in said channel in engagement with said heater.

10. The device defined in claim 1 wherein said member is a cellulose substrate having a rectangular configuration and impregnated with volatilizable pyrethrum insecticide.

* * * * *